US00PP25270P3

(12) United States Plant Patent
Khemakongkanond

(10) Patent No.: US PP25,270 P3
(45) Date of Patent: Jan. 27, 2015

(54) ***AGLAONEMA* PLANT NAMED 'KKAG201202'**

(50) Latin Name: *Aglaonema commutatum*
Varietal Denomination: KKAG201202

(71) Applicant: Kanachana Khemakongkanond, Bangkok (TH)

(72) Inventor: Kanachana Khemakongkanond, Bangkok (TH)

( * ) Notice: Subject to any disclaimer, the term of this patent is extended or adjusted under 35 U.S.C. 154(b) by 196 days.

(21) Appl. No.: 13/694,415

(22) Filed: Nov. 29, 2012

(65) Prior Publication Data

US 2014/0150148 P1 May 29, 2014

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — Annette Para

(57) ABSTRACT

A new and distinct *Aglaonema* cultivar named 'KKAG201202' is disclosed, characterized by large leaves and green-white petioles as well as a distinctive foliage variegation pattern unlike other known *Aglaonema* cultivers. The new variety is an *Aglaonema*, typically produced as an indoor ornamental plant.

1 Drawing Sheet

Latin name of the genus and species: *Aglaonema commutatum.*

Variety denomination: 'KKAG201202'.

BACKGROUND OF THE INVENTION

This application relates to a new cultivar of *Aglaonema commutatum*. The new variety is the product of a planned breeding program. The new variety originated as a seedling from the crossing of the unpatented, proprietary seed parent *Aglaonema commutatum* 'GBMD10' with the unpatented, proprietary pollen parent referred to as *Aglaonemac commutatum* 'KMK10'. The crossing was made by the inventor in commercial nursery during December of 2003.

The new variety was first selected by the inventor, Kanchana Khemakongkanond, a citizen of Thailand, in January of 2006, at the same nursery in Bangkok, Thailand. After identifying the new variety as a potentially interesting selection, the inventor continued confidential testing and propagation of 'KKAG201202', assessing stability of the unique characteristics of this variety.

Asexual reproduction of the new cultivar 'KKAG201202' by vegetative cuttings was first performed at the same nursery in Bangkok, Thailand during December of 2006. Subsequently at least three generations have been produced from vegetative cuttings, and have shown that the unique features of this cultivar are stable and reproduced true to type.

SUMMARY OF THE INVENTION

The cultivar 'KKAG201202' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KKAG201202'. These characteristics in combination distinguish 'KKAG201202' as a new and distinct *Aglaonema* cultivar:

1. Large leaves.
2. Distinctive foliage variegation pattern unlike other known *Aglaonema* cultivers.
3. Green-White petioles.

PARENT COMPARISON

Plants of the new cultivar 'KKAG201202' are similar to the seed parent, *Aglaonema* 'GBMD10' in most horticultural characteristics. The new variety, however, produces larger leaves and deeper foliage coloration than the seed parent.

Plants of the new cultivar 'KKAG201202' are similar to the pollen parent, *Aglaonema* 'KMK10' in most horticultural characteristics. Plants of the new variety, however, are easier and faster to grow.

COMMERCIAL COMPARISON

Plants of the new cultivar 'KKAG201202' are comparable to the unpatented variety *Aglaonema* 'Silver Bay'. The two *Aglaonema* varieties are similar in most horticultural characteristics; however, the new variety 'KKAG201202' produces less leaves and a different color pattern on the leaves. The petioles of 'KKAG201202' are green-white, whereas 'Silver Bay' produces a green petiole.

BRIEF DESCRIPTION OF THE PHOTOGRAPH

The accompanying photograph in FIG. 1 illustrates in full color a typical plant of 'KKAG201202' grown in a commercial greenhouse in Honselersdijk, The Netherlands. This plant is approximately 8 months old shown planted in 12 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'KKAG201202' plants grown according to the following protocols.

Plants were grown in Honselersdijk, the Netherlands under nursery conditions, with temperatures ranging approximately from 20° C. to 22° C. during the day and 18° C. to 20° C. at night with natural sunlight. Measurements and numerical values below represent averages of typical plant types.

Botanical classification: *Aglaonema Commutatum* 'KKAG201202'.

PROPAGATION

Propagation details:

*First propagation method*.—Cuttings.

*Type of propagation typically used*.—Cuttings.

*Time to initiate roots*.—About 14 days at approximately 21° C.

*Root description*.—Moderately dense, moderately thick, non-fibrous, fleshy, not free-branched, colored greyed-yellow; near RHS-CC 160B.

*Time to produce rooted plantlet*.—Approximately 10 weeks at approximately 19 to 23° C.

PLANT

Age of plant described: Approximately 8 months.

Growth habit: Upright with broad outwardly angled foliage.

Plant shape: Ovate.

Height: Approximately 19.9 cm to top of highest leaf.

Plant spread: Approximately 31.3 cm in a 12 cm circular pot.

Normal pot size: 12 cm circular pot.

Growth rate: Moderate.

Stem:

*Diameter*.—1.4 cm.

*Length*.—3.7 cm.

*Color*.—Yellow-green; near RHS-CC 145C, colored green around the leaf-buds; near RHS-CC 143A.

*Texture*.—Smooth, moderately glossy.

Branching characteristics: Basal clumping no lateral branches.

Number of clumps of leaves: 1.

Number of leaves per clump: Average 13.

Number of leaves per plant: Approximately 13.

FOLIAGE

Leaf:

*Arrangement*.—Distichous.

*Average length (excluding petiole)*.—Approximately 14.7 cm.

*Average width*.—Approximately 6.8 cm.

*Shape of blade*.—Ovate.

*Aspect*.—Leaves outward to slightly upright.

*Apex*.—Apiculate.

*Base*.—Rounded to very short attenuate.

*Margin*.—Entire.

*Texture of top surface*.—Smooth, moderately glossy.

*Texture of bottom surface*.—Smooth, slightly glossy.

*Color*.—Young foliage upper side: Green and greyed-green; near RHS-CC 138B and 191B, broadly and irregularly margined green; near Green RHS-CC 137B and 143A, main vein yellow-green; near RHS-CC 145B. Young foliage under side: Green to yellow-green; in between RHS-CC 143A and 146B, dotted yellow-green; near RHS-CC 145B and 145C, main vein yellow-green; near RHS-CC 145C. Mature foliage upper side: Greyed-green; near RHS-CC 190A and 191C. Broadly and irregularly margined green to yellow-green near RHS-CC N137A, 139A and 147A. Mature foliage under side: Greyed-green; near RHS-CC 193A, heavily dotted green; near RHS 143A.

Venation:

*Type*.—Pinnate.

*Venation coloration upper side*.—Green-white; near RHS-CC 157A.

*Venation coloration under side*.—White and green-white; RHS-CC 155D and 157D, both colors present.

Sheath:

*Average length*.—Approximately 5.6 cm.

*Average width*.—Approximately 0.6 cm.

*Color*.—Green-white; near RHS 157A, occasionally margined green; near RHS-CC 137A.

*Texture*.—Smooth, moderately glossy.

*Other distinguishing characteristics*.—N/A.

Petiole (excluding geniculum):

*Length*.—Approximately 6.8 cm.

*Width*.—At distal end: Approximately 0.5 cm. Above clump: Approximately 0.9 cm.

*Color*.—Green-white; near RHS 157D.

*Strength*.—Strong.

Geniculum:

*Length*.—Approximately 2.7 cm.

*Width*.—Approximately 0.5 cm.

*Color*.—Green-white; near RHS 157D.

*Other characteristics*.—No.

FLOWERING CHARACTERISTICS

Flowering not observed to date.

REPRODUCTIVE ORGANS

Not observed to date.

OTHER CHARACTERISTICS

Disease resistance: Good resistance to the normal diseases found in *Aglaonema*.

Drought tolerance and cold tolerance: Normal for species, USDA zone 10 and higher.

Fruit/seed production: No fruits/seeds detected to date.

What is claimed is:

1. A new and distinct cultivar of *Aglaonema* plant named 'KKAG201202' as herein illustrated and described.

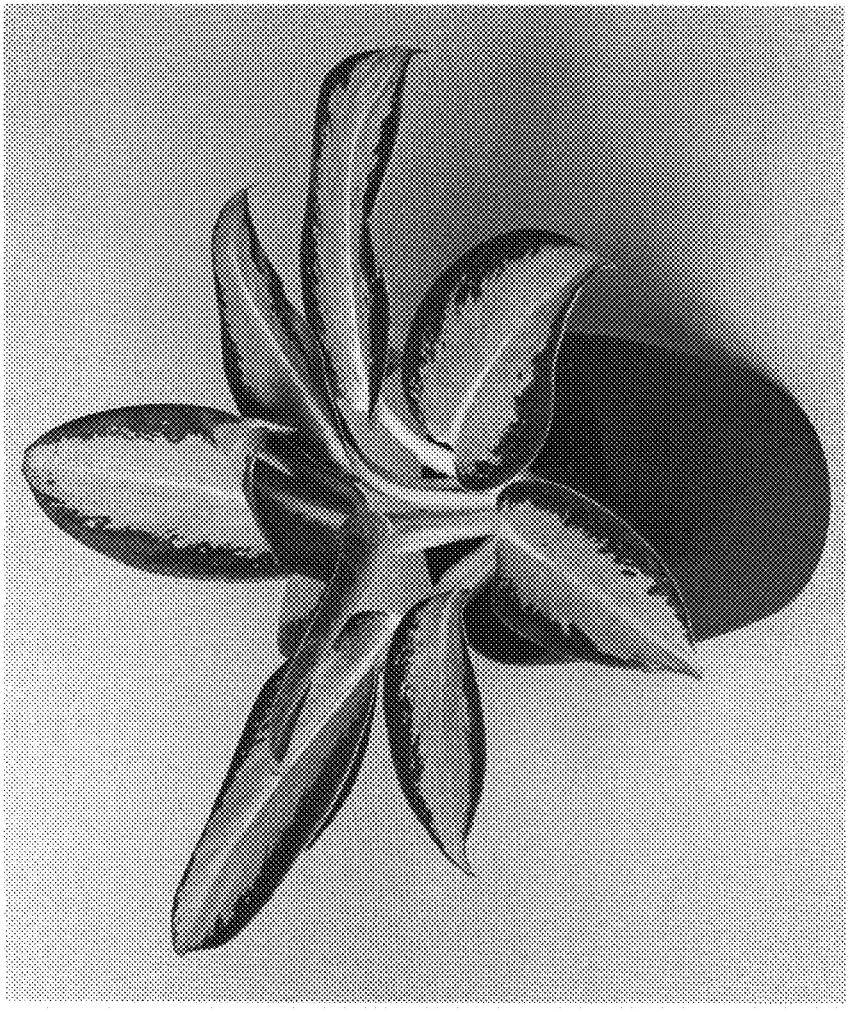

* * * * *